(12) United States Patent
IJpeij et al.

(10) Patent No.: US 7,547,751 B2
(45) Date of Patent: Jun. 16, 2009

(54) PROCESS FOR THE PREPARATION OF A POLYOLEFIN

(75) Inventors: Edwin IJpeij, Sittard (NL); Henricus Arts, Munstergeleen (NL); Gerardus van Doremaele, Sittard (NL); Felix Beijer, Sittard (NL); Francis van der Burgt, Herten (NL); Martin Zuideveld, Maastricht (NL)

(73) Assignee: DSM IP Assets B.V., Heerlen (NL)

( * ) Notice: Subject to any disclaimer, the term of this patent is extended or adjusted under 35 U.S.C. 154(b) by 361 days.

(21) Appl. No.: 10/567,097

(22) PCT Filed: Aug. 3, 2004

(86) PCT No.: PCT/EP2004/008710

§ 371 (c)(1),
(2), (4) Date: Jul. 3, 2006

(87) PCT Pub. No.: WO2005/014674

PCT Pub. Date: Feb. 17, 2005

(65) Prior Publication Data

US 2008/0153999 A1    Jun. 26, 2008

(30) Foreign Application Priority Data

Aug. 4, 2003 (EP) .................... 03077434
Apr. 1, 2004 (EP) .................... 04075990

(51) Int. Cl.
*C08F 4/642* (2006.01)
*C08F 4/649* (2006.01)
*C08F 4/6592* (2006.01)

(52) U.S. Cl. .................. 526/141; 526/156; 526/160; 526/165; 526/943; 502/123; 502/152; 502/155

(58) Field of Classification Search ............... 526/135, 526/161, 165, 156, 160; 502/103, 123, 152, 502/155
See application file for complete search history.

(56) References Cited

U.S. PATENT DOCUMENTS

| 6,245,871 B1 * | 6/2001 | Mackenzie et al. ......... 526/141 |
| 6,555,634 B1 | 4/2003 | Klosin et al. |
| 2001/0051587 A1 | 12/2001 | Williams |
| 2003/0004286 A1 | 1/2003 | Klosin et al. |
| 2003/0092563 A1 | 5/2003 | Gao et al. |
| 2003/0181317 A1 | 9/2003 | Tagge et al. |

FOREIGN PATENT DOCUMENTS

| CA | 2 243 726 | 1/2000 |
| EP | 0 644 206 | 3/1995 |
| EP | 0 874 005 | 10/1998 |
| EP | 0 881 233 | 12/1998 |
| EP | 0 940 408 | 9/1999 |
| EP | 0 990 664 | 4/2000 |
| EP | 1 026 180 | 8/2000 |
| WO | WO 96/13529 | 5/1996 |
| WO | WO 97/02298 | 1/1997 |
| WO | WO 98/45039 | 10/1998 |
| WO | WO 98/46651 | 10/1998 |
| WO | WO 00/32653 | 6/2000 |
| WO | WO 02/16374 | 2/2002 |
| WO | WO 02/070569 | 9/2002 |

OTHER PUBLICATIONS

Robyn K.J. Bott et al., "Monocyclopentadienyl phenoxy-imine and phenoxy-amine complexes of titanium and zirconium and their application as catalysts for 1-alkene polymerization"; Journal of Organometallic Chemistry, vol. 665, No. 1-2; Jan. 3, 2003; pp. 135-149.

Sei-ichi Ishii et al; "Zirconium complexes having phenoxy/cycloalkylimine chelate ligands for the polymerization of ethylene for vinyl-terminated low molecular weight polyethylenes"; The Chemical Society of Japan, vol. 7; 2002; pp. 740-741.

Jerald Feldman et al; "Electrophilic Metal Precursors and a β-Diimine Ligand for Nickel)II)- and Palladium (II)-Catalyzed Ethylene Polymerization"; Organometallics, vol. 16, No. 8; 1997; pp. 1514-1516.

Alfredo Martin et al; "Neutral and Cationic Group 4 Metal Compounds Containing Octamethyldibenzotetraazaannulene ($Me_8taa^{2-}$) Ligands. Synthesis and Reactivity of ($Me_8taa$)$MX_2$ and ($Me_8taa$)$MX^+$ Complexes (M=Zr, Hf; X=Cl, Hydrocarbyl, $NR_2$ OR)"; Organometallics, vol. 17, No. 3, 1998; pp. 382-397.

* cited by examiner

*Primary Examiner*—Caixia Lu
(74) *Attorney, Agent, or Firm*—Nixon & Vanderhye P.C.

(57) ABSTRACT

The invention related to a process for the polymerization of at least one aliphatic $C_{2-20}$ or aromatic $C_{4-20}$ hydrocarbyl mono- or multiolefin in the presence of a catalyst and an aluminum comprising co-catalyst, wherein the catalyst comprises a composition of a metal-organic reagent, a spectator ligand and optionally at least one equivalent of a hydrocarbylating agent. The invention further relates to a polymer obtainable by the process of the invention.

7 Claims, No Drawings

PROCESS FOR THE PREPARATION OF A POLYOLEFIN

This application is the U.S. national phase of international application PCT/EP2004/008710, filed 3 Aug. 2004, which designated the U.S. and claims benefit of EP 03077434.3, filed 4 Aug. 2003, and EP 04075990.4, filed 1 Apr. 2004, the entire contents of each of which are hereby incorporated by reference.

The invention relates to a process for the preparation of a polymer comprising at least one aliphatic or aromatic hydrocarbyl $C_{2-20}$ mono- or multiolefin in the presence of a catalyst and an aluminum comprising co-catalyst.

Such a process is described in EP416815.

EP416815 describes the preparation of a polymer of one or more aliphatic or aromatic hydrocarbyl $C_{2-20}$ mono- or diolefins in the presence of a catalyst consisting of a metal-organic compound and an aluminum comprising co-catalyst. An aluminum comprising co-catalyst is used because it results in a high reactivity of the catalyst system described in EP416815.

Disadvantage of the process described in EP416815 is the use of an expensive catalyst, which requires several reaction steps for its production. These processes require at least four steps: (i) reaction of a ligand with a strong base resulting in a metal-organic salt of this ligand, followed by (ii) contacting this salt with a metal-organic reagent resulting in a metal-organic compound which has optionally to (iii) be hydrocarbylated and (iv) further contacted with an aluminum comprising co-catalyst in order to form the active species. For some catalysts an additional oxidation step after the formation of the metal-organic compound is needed using an oxidizing agent.

An aim of the invention is to provide a process for the preparation of a polymer comprising one or more aliphatic or aromatic hydrocarbyl $C_{2-20}$ mono- or multiolefins in the presence of an aluminum comprising co-catalyst and a catalyst, which can be formed in situ in the polymerization equipment.

This aim is achieved in the process of the invention by a catalyst, which comprises a composition of a spectator ligand, a metal-organic reagent, and optionally at least one equivalent of a hydrocarbylating agent.

By the process of the invention a polymerization of one or more aliphatic or aromatic hydrocarbyl $C_{2-20}$ mono- or multiolefins in the presence of an aluminum comprising co-catalyst can be carried out in the presence of a catalyst, which is formed in situ in the polymerization equipment.

Processes for the preparation of a polymer of at least one aliphatic or aromatic hydrocarbyl $C_{2-20}$ olefins are fairly well known in the art. These processes are generally conducted by contacting at least one olefinic monomer with a catalyst comprising a metal-organic complex and a cocatalyst and optionally a scavenger in the gas phase or in the presence of an inert hydrocarbon solvent or diluent. Suitable solvents or diluents are a $C_{5-12}$ hydrocarbon which may be substituted by a $C_{1-4}$ alkyl group, such as pentane, hexane, heptane, octane, isomers and mixtures thereof, cyclohexane, methylcyclohexane, pentamethyl heptane and hydrogenated naphta. The process of the invention may be conducted at temperatures from about 20° C. to about 250° C., depending on the product being made.

An olefinic monomer is understood to be a molecule containing at least one polymerizable double bond.

Suitable olefin monomers may be $C_{2-20}$ olefins. Preferred monomers include ethylene and $C_{3-12}$ alpha olefins which are unsubstituted or substituted by up to two $C_{1-6}$ alkyl radicals, $C_{8-12}$ vinyl aromatic monomers which are unsubstituted or substituted by up to two substituents selected from the group consisting of $C_{1-4}$ alkyl radicals, $C_{4-12}$ straight chained or cyclic hydrocarbyl radicals which are unsubstituted or substituted by a $C_{1-4}$ alkyl radical. Illustrative non-limiting examples of such alpha-olefins are one or more of the α-olefins include propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 9-methyl-1-decene, 11-methyl-1-dodecene, 12-ethyl-1-tetradecene, (substituted) styrene, stilbene. These α-olefins may be used in combination.

The monomer may also be a polyene comprising at least two double bonds. The double bonds may be conjugated or non-conjugated in chains, ring-systems or combinations thereof, endo- and or exocyclic and may have different amounts and type of substituents. As result of that, a polyene may comprise of at least one aliphatic-, alicyclic- or aromatic group, or combinations thereof.

Generally, polyenes include aliphatic polyenes and alicyclic polyenes. More specifically, there can be mentioned aliphatic polyenes such as: 1,4-hexadiene, 3-methyl-1,4-hexadiene, 4-methyl-1,4-hexadiene, 5-methyl-1,4-hexadiene, 4-ethyl-1,4-hexadiene, 1,5-hexadiene, 3-methyl-1,5-hexadiene, 3,3-dimethyl-1,4-hexadiene, 5-methyl-1,4-heptadiene, 5-ethyl-1,4-heptadiene, 5-methyl-1,5-heptadiene, 6-methyl-1,5-heptadiene, 5-ethyl-1,5-heptadiene, 1,6-heptadiene, 1,6-octadiene, 4-methyl-1,4-octadiene, 5-methyl-1,4-octadiene, 4-ethyl-1,4-octadiene, 5-ethyl-1,4-octadiene, 5-methyl-1,5-octadiene, 6-methyl-1,5-octadiene, 5-ethyl-1,5-octadiene, 6-ethyl-1,5-octadiene, 1,6-octadiene, 6-methyl-1,6-octadiene, 7-methyl-1,6-octadiene, 6-ethyl-1,6-octadiene, 6-propyl-1,6-octadiene, 6-butyl-1,6-octadiene, 1,7-octadiene, 4-methyl-1,4-nonadiene, 5-methyl-1,4-nonadiene, 4-ethyl-1,4-nonadiene, 5-ethyl-1,4-nonadiene, 5-methyl-1,5-nonadiene, 6-methyl-1,5-nonadiene, 5-ethyl-1,5-nonadiene, 6-ethyl-1,5-nonadiene, 6-methyl-1,6-nonadiene, 7-methyl-1,6-nonadiene, 6-ethyl-1,6-nonadiene, 7-ethyl-1,6-nonadiene, 7-methyl-1,7-nonadiene, 8-methyl-1,7-nonadiene, 7-ethyl-1,7-nonadiene, 1,8-nonadiene, 5-methyl-1,4-decadiene, 5-ethyl-1,4-decadiene, 5-methyl-1,5-decadiene, 6-methyl-1,5-decadiene, 5-ethyl-1,5-decadiene, 6-ethyl-1,5-decadiene, 6-methyl-1,6-decadiene, 6-ethyl-1,6-decadiene, 7-methyl-1,6-decadiene, 7-ethyl-1,6-decadiene, 7-methyl-1,7-decadiene, 8-methyl-1,7-decadiene, 7-ethyl-1,7-decadiene, 8-ethyl-1,7-decadiene, 8-methyl-1,8-decadiene, 9-methyl-1,8-decadiene, 8-ethyl-1,8-decadiene, 1,9-decadiene, 1,5,9-decatriene, 6-methyl-1,6-undecadiene, 9-methyl-1,8-undecadiene and 1,13-tetradecadiene, 1,3-butadiene, isoprene.

Alicyclic polyenes may consist of at least one cyclic fragment. Particular examples of these alicyclic polyenes include: vinylcyclohexene, vinyinorbornene, ethylidene norbornene, dicyclopentadiene, cyclooctadiene, 2,5-norbornadiene, 1,4-divinylcyclohexane, 1,3-divinylcyclohexane, 1,3-divinylcyclopentane, 1,5-divinylcyclooctane, 1-allyl-4-vinylcyclohexane, 1,4-diallylcyclohexane, 1-allyl-5-vinylcycloocatane, 1,5-diallylcyclooctane, 1-allyl-4-isopropenylcyclohexane, 1-isopropenyl-4-vinylcyclohexane and 1-isopropenyl-3-vinylcyclopentane, 1,4-cyclohexadiene Preferred polyenes are polyenes having both at least one endocyclic and optionally at least one exocyclic double bond, like 5-methylene-2-norbornene and 5-ethylidene-2-norbornene, 5-vinylnorbornene, and bicyclo-(2,2,1)-hepta-2,5-diene), dicyclopentadiene, vinylcyclohexene.

Examples of aromatic polyenes include divinylbenzene (including its isomers), trivinylbenzene (including its isomers), vinylisopropenylbenzene (including its isomers), vinylindene (including its isomers) and allylindene (including its isomers).

All above mentioned monomers may be further substituted with at least one group comprising a heteroatom of group 13-17 or combinations thereof.

Homo-, co- and ter-polymers of the above mentioned olefinic monomers and blends thereof can be prepared with the process of the present invention.

Other olefin polymers which may be prepared in accordance with the present invention may be determined by one of ordinary skill in the art using non-inventive testing.

In the process of the invention an aluminum comprising co-catalyst is used. An aluminum comprising co-catalyst is understood to be a cocatalyst as described in *Chem. Rev.*, 2000, 100, 1391 by E. Y-X. Chen and T. J. Marks.

In the process of the invention the metal-organic reagent can be represented by formula 1:

$$ML_jX_p \qquad \text{(formula 1)}$$

with M being a metal from group 3-11, X a monoanionic ligand bonded to M, L a neutral Lewis basic ligand bonded to M, j representing an integer denoting the number of neutral ligands L and p is the valency of the metal M.

Examples of Lewis basic ligands include ethers, such as tetrahydrofuran (THF), diethylether, thioethers, like thiophene, diethylsulfide, dimethylsulfide, amines, such as trialkylamines, pyridine, bipyridine, TMEDA, (−)-sparteine), phosphanes and diphosphanes, such as triphenylphoshine, trialkylphosphanes, bidentate alkyl or aryidiphosphanes). The amount of ligands (X and L) depends on the valency of the metal and the stability of the metal-organic reagent. The metal-organic reagent may be monomeric, oligomeric or a cluster. The number of anionic ligands equals the valency of the metal used. The number of neutral ligands on the metal-organic reagent may range from 0 to the amount that satisfies the 18-electron rule, as known in the art.

Each anionic ligand, X, may be independently selected from the group consisting of monoanionic spectator ligands, hydride, halide, alkyl, silyl, germyl, aryl, amide, aryloxy, alkoxy, phosphide, sulfide, acyl, pseudo halides such as cyanide, azide, acetylacetonate, etc., or a combination thereof. Preferably, X is hydride or a moiety selected from the group consisting of monoanionic spectator ligands, halide, alkyl, aryl, silyl, germyl, aryloxy, alkoxy, amide, siloxy and combinations thereof (e.g. alkaryl, aralkyl, silyl substituted alkyl, silyl substituted aryl, aryloxyalkyl, aryloxyaryl, alkoxyalkyl, alkoxyaryl, amidoalkyl, amidoaryl, siloxyalkyl, siloxyaryl, amidosiloxyalkyl, haloalkyl, haloaryl, etc.) having up to 20 non-hydrogen atoms.

The process of the invention is optionally carried out in the presence of at least one equivalent of an hydrocarbylating agent. In the process of the invention hydrocarbylating agents are nucleophilic groups comprising a metal-, or a metalloid-carbon or hydride bond. The number of equivalents required for the process of the invention depends on the amount and the type (mono-, or dianionic) of the spectator ligand.

Examples of hydrocarbylating agents are: tri-, or tetrahydrocarbyl boron, tri-, or tetrahydrocarbyl aluminum, tri-, or tetrahydrocarbyl gallium, tri-, or tetrahydrocarbyl indium and di-, or tetrahydrocarbyl tin, or the reaction products of these hydrocarbylating agents with sterically hindered alcohols, thiols, amines or phosphanes.

Preferably the hydrocarbylating agent comprises a metal or a metalloid chosen from group 1, 2, 11, 12, 13 or 14. Examples of hydrides from metals or metalloids of group 1, 2, 11, 12, 13, 14 include: lithiumhydride, sodiumhydride, potassiumhydride, calciumhydride, magnesiumhydride, copperhydride, zinchydride, cadmiumhydride, borane, aluminumhydride, galliumhydride, siliconhydride, germaniumhydride, and tinhydride.

Preferably the hydrocarbylating agent comprises Li, Mg, Zn, or Al.

Examples of Li comprising hydrocarbylating agents are methyllithium, phenyllithium, benzyllithium, biphenyllithium, naphtyllithium, lithio-dimethylresorcinol, and lithio-N,N-dimethylaniline.

Examples of magnesium comprising hydrocarbylating agents are methylmagnesiumhalide, phenylmagnesiumhalide, benzylmagnesiumhalide, biphenylmagnesiumhalide, naphtylmagnesiumhalide, tolylmagnesiumhalide, xylylmagnesiumhalide, mesitylmagnesiumhalide, dimethylresorcinolmagnesiumhalide, N,N-dimethylanilinemagnesiumhalide, dimethylmagnesium, diphenylmagnesium, dibenzylmagnesium, (biphenylene)magnesium, dinaphtylmagnesium, ditolylmagnesium, dixylylmagnesium, dimesitylmagnesium, bis(dimethylresorcinol)magnesium, and bis(N,N-dimethylaniline)magnesium.

Examples of aluminum comprising hydrocarbylating agents are diisobutylaluminum hydride, $C_1$-$C_{20}$ trihydrocarbyl aluminum, and hydrocarbylaluminoxanes.

To facilitate the process of the invention, the process may be carried out in the presence of a base other than a hydrocarbylating agent. Examples of such bases include, amines, phosphanes, carboxylates (for example potassium acetate), hydroxides, cyanides, amides and carbonates of Li, Na, K, Rb, Cs, ammonium and the group 2 metals Mg, Ca, and Ba, the alkali metal (Li, Na, K, Rb, Cs) phosphates and the phosphate esters (eg. $C_6H_5$ OP(O)(ONa)$_2$ and related aryl and alkyl compounds) and their alkoxides and phenoxides, thallium hydroxide, alkylammonium hydroxides, hydrides from metals or metalloids of group 1, 2, 11, 12, 13, 14. Also the metallic alkalimetals of group 1 may be applied as a base.

In the process of the invention a spectator ligand is chosen from a monoacidic spectator ligand, a diacidic bidentate spectator ligand, a monoacidic bidentate spectator ligand, or a Lewis basic bi-, or multidentate spectator ligand.

An example of a mono acidic spectator ligand is an imine ligand according to formula 2, or the HA adduct thereof, wherein HA represents an acid, of which H represents its proton and A its conjugate base, $$Y=N-R \qquad \text{(formula 2),}$$

wherein Y is selected from a substituted carbon, nitrogen or phosphorous atom and R represents a substituent. If Y represents a substituted carbon atom, the number of substituents is 2. If Y represents a substituted nitrogen atom, the number of substituents is 1 and the number of substituents is 1 or 3 if Y represents a phosphorous atom, depending on the valency of the phosphorous atom.

Substituents on carbon, nitrogen or phosphorous may be equal or different, optionally linked with each other, optionally having hetero atoms. Substituents may be protic or aprotic.

A protic substituent is defined here as a substituent which has at least one group 15 or group 16 atom containing at least one proton.

Examples of protic subsituents include $C_1$-$C_{20}$ linear, branched or cyclic hydrocarbyl radicals, substituted with a group 15 or 16 atom bearing at least one hydrogen atom. Preferred protic substituents include phenolic radicals, pyrrolic radicals, indolic radicals, and imidazolic radicals.

The substituent is called aprotic if the substituent lacks a group containing a group 15 or group 16 atom bearing a proton. An unsubstituted aprotic hydrocarbyl radical can be a $C_1$-$C_{20}$ linear, branched or cyclic radical, a hydrogen atom, a halogen atom, a group 14 oxy radical—such as a $C_{1-8}$ alkoxy radical, a $C_{6-10}$ aryl or aryloxy radical, silyloxy radical, germanyloxy radical, stannyloxy radical—an amido radical, or a $C_{1-20}$ hydrocarbyl radical unsubstituted or substituted by a halogen atom, a $C_{1-8}$ alkoxy radical, a $C_{6-10}$aryl or aryloxy radical, an amido radical, a silyl radical of the formula:

(formula 3)

or a germanyl radical of the formula:

(formula 4)

wherein $R^{2j}$ with j=1 to 3 is independently selected from the group consisting of hydrogen, a $C_{1-8}$alkyl or alkoxy radical, $C_{6-10}$aryl, aryloxy radicals a silyl radical of formula 3 or a germanyl radical of formula 4, each substituent $R^{2j}$ may be linked with another $R^{2j}$ to form a ring system.

The substituent R can be H, or being equal as these for the protic substituent on Y.

Examples of imine ligands according to formula (2) include: guanidines, iminoimidazolines, phosphinimines, phenolimines, pyrroleimines, indoleimines and imidazoleimines.

R may be linked with Y, thus forming a ring system, optionally comprising hetero atoms, or optionally comprising functional groups. Examples of ligands comprising such ring systems include: 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole.

In the process of the invention, HA represents an acid, of which H represents its proton and A its conjugate base. Examples of A are halogenides, (such as fluoride, chloride, bromide, or iodide), sulfate, hydrogensulfate, phosphate, hydrogenphosphate, dihydrogenphosphate, carbonate, hydrogencarbonate, aromatic or aliphatic carboxylates, cyanide, tetrafluoroborate, (substituted) tetraphenylborates, fluorinated tetraarylborates, alkyl or aryl sulfonates.

In case the HA adduct of the imine ligand is used, one more equivalent of the hydrocarbylating agent is required.

Examples of mono- or diacidic spectator ligand are ligands according to formula 5:

$(HA_1)_q(-Z-)_n(A_2H)_r$   (formula 5), wherein $A_1$ and $A_2$ are monoacidic cyclopentadienyl comprising ligands (Cp), with q and r representing an integer denoting the number of Cp ligands with q+r=1 or 2, optionally linked by n bridging groups Z, with n representing the number of parallel bridges Z, $A_1$, $A_2$ when bonded via Z together forming a bidentate diacidic spectator ligand or if Z is absent $A_1$, $A_2$ form two monoacidic spectator ligands.

The ligands $A_1$ and $A_2$ are defined as cyclopentadienyl comprising ligands. Under cyclopentadienyl comprising ligands is understood that a part of the molecular structure contains a cyclopentadienyl (Cp) ring. This ring may be substituted with at least one R'-group. When the Cp-ring is substituted with at least two R' groups, these R' groups may form ring systems. As result of that the Cp-comprising ligand may be indenyl comprising ligands or fluorenyl comprising ligands. The ligands $A_1$ and $A_2$ may be each independently selected (substituted) cyclopentadienyl groups, (substituted) indenyl groups, (substituted)fluorenyl groups, (substituted) tetrahydroindenyl groups, (substituted) tetrahydrofluorenyl groups, (substituted) octahydrofluorenyl groups, (substituted) benzoindenyl groups, (substituted) heterocyclopentadienyl groups, (substituted) heteroindenyl groups, (substituted) heterofluorenyl groups, or its isomers. Here and in the following a hetero cyclopentadienyl group (in the following also referred to as 'hetero ligand') is understood to be a group that has been derived from a cyclopentadienyl group, but in which at least one of the C atoms in the 5-ring of the cyclopentadienyl has been replaced by a hetero atom, which hetero atom may be chosen from group 14, 15 or 16. If there is more than one hetero atom present in the 5-ring of the hetero ligand, these hetero atoms may be either the same or different. More preferably, the hetero atom has been chosen from group 15, while yet more preferably the hetero atom is phosphorus.

The R' groups may each independently be hydrogen or a hydrocarbon radical with 1-20 carbon atoms (e.g alkyl, aryl, biaryl, aralkyl, alkaryl and the like) or a heteroatom comprising moiety from group 13-17. Examples of such hydrocarbon radicals are methyl, ethyl, n-propyl, i-propyl, butyl (including isomers), hexyl (including isomers), decyl (including isomers), phenyl, biphenyl (including isomers) and the like. Examples of heteroatom comprising moieties of group 13-17 include borane radicals, silyl radicals, germyl radicals, stannyl radicals, amide radicals, phosphide radicals, oxide radicals, sulphide radicals, halide radicals, halide substituted hydrocarbyl radicals and the like. Also, two adjacent hydrocarbon radicals may be connected with each other in a ring system. Such a group as well may contain one or more R' groups as substituents. R' may also be a substituent which instead of or in addition to carbon and/or hydrogen may comprise one or more hetero atoms of groups 13-17.

The bridging group Z may contain $sp^3$, $sp^2$ or sp hybridized atoms of group 13 to 16 or combinations thereof. The bridging group Z may consist of linear, cyclic fragments, spiro ring systems, or combinations thereof. Examples of a carbon containing Z group may each separately be a hydrocarbon group with 1-20 carbon atoms, e.g. alkylidene, arylene, biarylene, aryl alkylidene, etc. Examples of such groups are methylene, ethylene, propylene, butylene, phenylene, naphtylene, biphenylene, binaphtylene. Examples of silicium containing groups are dimethylsilyl, diethylsilyl, dipropylsilyl, including its isomers, (substituted) diphenylsilyl, dimethoxysilyl, diethoxysilyl, dipropoxysilyl, and diphenoxysilyl.

An example of a diacidic bidentate spectator ligand or a monoacidic bidentate spectator ligand is a ligand according to formula 6:

$HA_1$-Z-D(H)$_b$   (formula 6)

in which $A_1$ is a delocalized $\eta^5$ bonding cyclopentadienyl comprising ligand, Z is a moiety comprising boron, or a member of Group 14, and optionally also sulfur or oxygen, said moiety having up to 20 non-hydrogen atoms, and optionally $A_1$ and Z together form a fused ring system, D is a Lewis basic ligand bonded to Z comprising a group 15 or 16 atom having up to 20 non-hydrogen atoms, optionally D and Z together form a fused ring system and b=0 or 1. Hereinafter a Lewis basic ligand is also referred to as a donor moiety. The mono-, or diacidic spectator ligand has 1 or 2 acidic protons, one of which is the acidic cyclopentadienyl proton. If the acidic spectator ligand contains only 1 proton (thus the cyclopentadienyl acidic proton), then b equals 0 and D is a neutral two electron donor moiety. If the acidic spectator ligand contains 2 protons, than b equals 1 and D contains an acidic proton.

Preferably D is —O—, —S—, —NR*-, —PR*-, or a neutral two electron donor moiety selected from the group consisting of OR*, SR*, NR*$_2$, or PR*$_2$.

Z may be SiR*$_2$, CR*$_2$, SiR*$_2$SiR*$_2$, CR*$_2$CR*$_2$, CR*=CR*, CR*$_2$SiR*$_2$, GeR*$_2$, BR*, BR*$_2$; wherein each R* can be independently selected from the group consisting of hydrogen, alkyl, aryl, silyl, halogenated alkyl, halogenated aryl radicals, or combinations thereof (e.g. aralkyl, alkaryl, haloalkaryl and haloaralkyl radicals) having up to 20 non-hydrogen atoms, or two or more R* groups from Y, Z, or both Y and Z form a fused ring system.

Another example of a monoacidic bidentate ligand (SH) is a) is a bi- or multidentate ligand, wherein S is represented by formula 7:

$(Ar-Z-)_sY(-Z-DR'_n)_q$,     (formula 7)

with,

Y represents an anionic moiety of S, Z optional bridging groups between the Y moiety and the DR'$_n$ and/or Ar group, D a hetero atom chosen form group 15 or 16, R' an optional substituent, Ar an electron-donating aryl group, n the number of R' groups bonded to D, and q and s are integers with q+s≧1.

If the ligand is a ligand represented by $(Ar-Z-)_sY(-Z-DR'_n)_q$, the transition metal is preferably chosen from groups 4-6 of the Periodic Table of the Elements. More preferably, the transition metal has been chosen from group 4, with the most preference to titanium (Ti) as transition metal. The transition metal is preferably present in reduced form in the compound, which means that the transition metal is in a reduced oxidation state (p). By 'reduced oxidation state' is meant an oxidation state which is lower than the highest possible oxidation state for a particular metal, which means at most $M^{3+}$ for a transition metal of group 4, at most $M^{4+}$ for a transition metal of group 5 and at most $M^{5+}$ for a transition metal of group 6.

Examples of Y moieties include hydrocarbyl substituted groups comprising a group 15 or 16 atom, (substituted) cyclopentadienyl, (substituted) indenyl, (substituted) fluorenyl, (substituted) heterocyclopentadienyl, (substituted) heteroindenyl, (substituted) heterofluorenyl, or imine groups. Imine groups are defined as groups containing a double bonded nitrogen atom. Examples of imine groups are ketimide, guanidine, phosphinimide, iminoimidazoline, (hetero)aryloxyimines, pyrroleimines, indoleimines, imidazoleimines or (hetero)aryloxides, (substituted) pyridin-2-yl-methoxy, (substituted) quinolin-2-yl-methoxy, 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole and the like.

The optional bridging group Z may contain sp$^3$, sp$^2$ or sp hybridized atoms or combinations thereof. The bridging group Z may consist of linear, cyclic fragments, or combinations thereof. The Z groups may each separately be a hydrocarbon group with 1-20 carbon atoms, e.g. alkylidene, arylene, aryl alkylidene, etc. Examples of such groups are methylene, ethylene, propylene, butylene, biphenylene, binaphtylene, phenylene, whether or not with a substituted side chain, linear or cyclic.

Besides carbon, the main chain of the Z group may also contain larger members of group 14, such as silicon, germanium or tin. Examples of such Z groups are: dialkyl silylene, dialkyl germylene, tetra-alkyl disilylene or tetraalkyl silaethylene (—SiR'$_2$CR'$_2$).

The hetero atom containing donor group DR'$_n$ consists of at least one group 15 or group 16 atom, or a combination thereof. Examples of donor groups include imine groups as defined above, amine groups, phosphane groups, ether groups, or thioether groups.

Also, Y, Z and D may be part of an aromatic ring system, optionally containing sp$^3$, sp$^2$ or sp hybridized atoms or combinations thereof, together forming a spectator ligand. The D atom may thus be a part of the bridging group. In this case, the D atom containing bridging group may be further substituted by at least one optional bridging group Z containing donor groups DR'$_n$. Examples of spectator ligands containing aromatic ring systems having a donor atom D in the bridging group Z include (hetero)aryloxyimines, pyrroleimines, indoleimines, imidazoleimines or (hetero)aryloxides, (substituted) pyridin-2-methylenoxy, (substituted) quinolin-2-methylenoxy, 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole.

Preferably, the Y moiety may be an amido (—NR'-) group, a phosphido (—PR'-) group, an imine group, a (substituted) cyclopentadienyl group, a (substituted) indenyl group, a fluorenyl group, a (substituted) heterocyclopentadienyl group, a (substituted) heteroindenyl group, and a (substituted) heterofluorenyl group, Here and in the following a hetero cyclopentadienyl group (in the following also referred to as 'hetero ligand') is understood to be a group that has been derived from a cyclopentadienyl group, but in which at least one of the C atoms in the 5-ring of the cyclopentadienyl has been replaced by a hetero atom, which hetero atom may be chosen from group 14, 15 or 16 of the Periodic Table of the Elements. If there is more than one hetero atom present in the 5-ring of the hetero ligand, these hetero atoms may be either the same or different. More preferably, the hetero atom has been chosen from group 15, while yet more preferably the hetero atom is phosphorus.

Preferably, the electron donor group DR'$_n$ consists of a hetero atom D, chosen from group 15 or 16, and one or more substituents R' bonded to D. The number of R' groups is linked up with the nature of the hetero atom D, in the sense that n=2 if D is from group 15 and n=1 if D is from group 16. The substituent R' bonded to D is as defined. The hetero atom D has preferably been chosen from the group comprising nitrogen (N), oxygen (O), phosphorus (P) and sulphur (S); more preferably, the hetero atom is nitrogen (N) or phosphorus (P). It is further possible for two R' groups in the DR'$_n$ group to be connected with each other to form a ring-shaped structure (so that the DR' group can be a pyrrolidinyl group). The DR'$_n$ group can form coordinative bonds with M.

The aromatic electron-donating group (or donor), Ar, used can be substituted or non-substituted aryl group (C$_6$R'$_5$), such as phenyl, tolyl, xylyl, mesitylyl, cumyl, tetramethyl phenyl, pentamethyl phenyl, etc. The Ar group may also contain at least one heteroatom from group 15 or group 16. Examples of such heteroatom containing Ar groups are (substituted) pyrrole, (substituted) pyridine, (substituted) thiophene, (substituted) furan. The coordination of this Ar or heteroatom containing Ar group in relation to M may vary from $\eta^1$ to $\eta^6$.

The R' groups may each separately be hydrogen or a hydrocarbon radical with 1-20 carbon atoms (e.g. alkyl, aryl, aryl alkyl and the like). Examples of such hydrocarbon radicals are methyl, ethyl, propyl, butyl, hexyl, decyl, phenyl and the like. Also, two adjacent hydrocarbon radicals may be connected with each other in a ring system. As result from that, the Cp group may be an indenyl, tetrahydroindenyl, a fluorenyl, a tetrahydrofluorenyl, an octahydrofluorenyl or a benzoindenyl group. Such a group as well may contain one or more R' groups as substituents. R' may also be a substituent which instead of or in addition to carbon and/or hydrogen may comprise one or more hetero atoms of groups 14-16. Thus, a substituent may be a Si-containing group.

An example of a Lewis basic bi- or multidentate ligand is a ligand according to formula 8:

R-D-(Z-D)$_n$-R    (formula 8)

wherein Z is a bridging group, between two donor atom containing groups (D),

D a group comprising a hetero atom chosen from group 15 or 16, and R is a substituent. For all clarity, the ligand of formula 8 is not the same ligand as the ligand (L) in the metal-organic reagent. Examples of a Lewis basic bi-, or multidentate ligand are di-imines, tri-imines and di-imines comprising an aromatic group comprising a hetero atom of group 15 or 16.

If a ligand according to formula 8 is used, the metal of the metal-organic reagent preferably is a metal from group 7-11.

The process of the invention can be carried out in a broad variety of polymerization equipment. It can be carried out in a single reactor, or in multiple reactors, in series or parallel and combinations thereof. The process can be carried out in gasphase, bulk, or in suspension/slurry as a batch or continuous process.

The process of the invention is preferably carried out in a solvent. Suitable solvents are solvents that do not react with the metal-organic reagent or the metal-organic compound formed in the process of the invention. Examples of suitable solvents include aromatic and aliphatic hydrocarbons, halogenated hydrocarbons, or mixtures thereof.

The process of the invention can be carried out in different ways, which can be distinguished by the sequence in which the spectator ligand, the metal-organic reagent, the hydrocarbylating agent and the aluminum comprising co-catalyst are added to a polymerization reactor. Preferably the spectator ligand, the metal-organic reagent, the hydrocarbylating agent and the aluminum comprising co-catalyst are each added as a solution or a suspension to the process of the invention.

One way is to add the spectator ligand, the metal-organic reagent, the hydrocarbylating agent and the aluminum comprising co-catalyst directly to the polymerization reactor.

Another way is that the spectator ligand, the metal-organic reagent and the hydrocarbylating agent are premixed before the reactor. The advantage of premixing the spectator ligand, the metal-organic reagent and the hydrocarbylating agent is that this can be done under conditions of temperature, concentration and time different from those in the polymerization reactor, thus leading to a more active catalyst.

In this way the aluminum comprising co-catalyst can be added to the thus formed mixture either before the reactor or parallel to this mixture direct into the reactor. Adding the aluminum comprising co-catalyst to the above mentioned premixture has the advantage that an active catalyst system can be formed in a more concentrated environment than in the reactor. An even more active catalyst can be obtained by mixing the metal-organic reagent with the spectator ligand before the addition of the hydrocarbylating agent.

The invention is further related to a polymer obtainable with the process of the invention and in particular obtainable with a process using a spectator ligand (Ar-Z-)$_s$Y(-Z-DR'$_n$)$_q$, wherein Z is an optional bridging groups between an anionic moiety Y and the DR'$_n$ and/or Ar group, D a hetero atom chosen form group 15 or 16, R' an optional substituent, Ar an electron-donating aryl group, n the number of R' groups bonded to D, q and s integers with q+s≧1 and wherein Y is an imine group. Preferably the imine is a ketimide, phosphinimide, guanidine, or iminoimidazoline. Other preferred imines are spectator ligands wherein Y, R and D are part of an aromatic ring system, optionally containing sp$^3$, sp$^2$ or sp hybridized atoms or combinations thereof. Examples of these imines include: (hetero)aryloxyimine (like (substituted) derivatives of phenoxyimines, pyrroleimines, hydroyquinolines and the like) (hetero)arylsulphidoimine, (hetero) arylphosphidoimine and (hetero)arylamidoimine.

The invention also relates to a polymer obtainable with the process of the invention wherein Y is an imine and wherein the donor D is a ketimine, phosphinimine, guanidine, or iminoimidazoline.

The invention further relates to a polymer obtainable with the process of the invention using a spectator ligand (Ar-Z-)$_s$ Y(-Z-DR'$_n$)$_q$, wherein Y represents an anionic moiety of S, Z is an optional bridging groups between the Y moiety and the DR'$_n$ and/or Ar group, D a hetero atom chosen form group 15 or 16, R' an optional substituent, Ar an electron-donating aryl group, n the number of R' groups bonded to D, q and s integers with q+s≧1 and, and wherein D is a ketimide, phosphinimide, guanidine, or an iminoimidazoline.

EXAMPLES

Polymerisation Equipment.

The batch copolymerisation was carried out in a polymerisation equipment, having a catalyst dosing vessel equipped with a catalyst dosing pump for the addition of the catalyst to a 2-liter batch autoclave equipped with a double intermig stirrer and baffles. The reactor temperature was controlled by a Lauda Thermostat. The feed streams (solvents and monomers) were purified by contacting them with various absorption media as is known in the art. During polymerisation, the ethylene (C2) and propylene (C3) were continuously fed to the gas cap of the reactor. The pressure of the reactor was kept constant by means of a back-pressure valve.

Copolymerisation Experiments.

In an inert atmosphere of nitrogen, the reactor was filled with pentamethylheptanes (PMH) (950 mL) and an amount of MAO (Crompton 10 wt % in toluene) and 4-methyl-2,6-di-tert-butylphenol (BHT) as given in Tables 1 and 2. The reactor was heated to 90° C., while stirring at 1350 rpm. The reactor then was pressurized to 0.7 MPa and kept under a determined flow of 200 NL/h of ethylene and 400 NL/h of propylene for 15 minutes. Then, the catalyst components were added to the reactor and possible residual material was rinsed with PMH (50 mL) and subsequently fed to the reactor.

After 10 minutes of polymerisation, the monomer flow was stopped and the solution was slowly poured into a 2 L Erlenmeyer flask, and dried over-night at 100° C. under reduced pressure.

The polymers were analysed by FT-IR to determine the amount of incorporated C3 and Intrinsic Viscosity being an indication for the average molecular weight.

Polymer Analysis.

The amount of incorporated C3 in weight per cents relative to the total composition, was measured by means of Fourier transformation infrared spectroscopy (FT-IR) according to ASTM D 3900 method A.

The Intrinsic Viscosity (IV) was measured at 135° C. in decaline.

Examples 1-15

In Situ Polymerisation

These catalysts were prepared in the polymerisation equipment by adding amounts as depicted in table 1a of toluene solutions of the metal-organic reagent, the ligand and the base successively to the catalyst dosing vessel in toluene (15 mL). After stirring for 5 minutes the mixture was injected into the polymerisation reactor. Results are shown in Table 1 b.

The experiments 1, 2, 5, 12 and 13 were carried by adding a prepared and purified metal-organic compound to the catalyst dosing vessel, and subsequently fed to the polymerisation reactor.

It can be concluded from the comparison of all experiments with experiment 2, that all in situ prepared catalysts produce copolymers having a higher molecular weight than the copolymer produced with the CpTiCl₃ and base only, which allows polymerisation of a polyolefin by just adding a metal-organic reagent, an imine ligand and at least 1 equivalent of a base to the polymerisation equipment.

From Examples 8 and 10 it can be concluded that a process in the presence of between 5 and 10 equivalents of the imine ligand according to formula 1 is mostly preferred.

TABLE 1b

In situ polymerisations: polymerisation results

| Example | ΔT (°C.) | Yield (g) | residual Ti in polymer (ppm) | Incorporated $C_3^=$ (wt %) | IV (dl/g) |
|---|---|---|---|---|---|
| 1 | 0.8 | 2.93 | 8.2 | 41 | 2.4 |
| 2 | 0.5 | 2.74 | 13.1 | 62 | 0.96 |
| 3 | 3.5 | 8.97 | 5.3 | 46 | Nd |
| 4 | 1.6 | 5.34 | 3.6 | 42 | Nd |
| 5 | 1.8 | 6.09 | 0.4 | 48 | 2.77 |
| 6 | 2.0 | 8.41 | 4.3 | 54 | 2.07 |
| 7 | 0.8 | 3.76 | 9.5 | | |
| 8 | 4.2 | 14.37 | 2.5 | 51 | 2.32 |
| 10 | 4.9 | 19.84 | 0.6 | 52 | 2.29 |
| 11 | 4.4 | 18.05 | 1.1 | 50 | |
| 12 | 0.6 | 0 | | | |
| 13 | 1.3 | 3.55 | 67.4 | | 1.67 |
| 14 | 1.1 | 3.18 | 75.3 | | 1.65 |
| 15 | 1.2 | 2.89 | 82.8 | | 1.72 |

The invention claimed is:

1. A process comprising polymerizing at least one aliphatic $C_{2-20}$ hydrocarbyl mono- or multiolefin in the presence of a catalyst and an aluminum-comprising co-catalyst, wherein the catalyst is a composition comprising a metal-organic reagent, a spectator ligand and optionally at least one equivalent of a hydrocarbylating agent, and wherein the metal organic reagent is represented by $ML_jX_p$, where M is Ti, X is a monoanionic ligand bonded to M, L is a neutral ligand bonded to M, j represents an integer denoting the number of neutral ligands L, and p is the valence of the metal M, and wherein the spectator ligand is an imine ligand or an HA adduct thereof, wherein HA represents an acid of which H represents its proton and A represents its conjugate base.

TABLE 1a

In situ polymerisations: polymerisation conditions

| Example | Metal-organic reagent/ compound | Metal-organic compound dosage (μmol Ti) | ligand | Ligand dosage (μmol) | Base | Base dosage (μmol) | Activator system | Al/Ti Molar ratio | BF20/Ti Molar ratio | BHT/Al Molar ratio | Pol. Time (min) |
|---|---|---|---|---|---|---|---|---|---|---|---|
| 1 | 1 | 0.5 | — | — | — | — | MAO/BHT | 600 | | 2 | 10 |
| 2 | CpTiCl3 | 0.75 | — | — | Et3N | 0.75 | MAO/BHT | 3000 | — | 1 | 10 |
| 3 | CpTiCl3 | 1.0 | L1 | 2.0 | Et3N | 1.0 | MAO/BHT | 3000 | — | 1 | 10 |
| 5 | 2 | 0.05 | — | — | — | — | MAO/BHT | 3000 | — | 1 | 10 |
| 6 | CpTiCl3 | 0.75 | L2 | 1.5 | Et3N | 0.75 | MAO/BHT | 3000 | — | 1 | 10 |
| 7 | CpTiCl3 | 0.75 | L2 | 0.75 | Et3N | 0.75 | MAO/BHT | 3000 | — | 1 | 10 |
| 8 | CpTiCl3 | 0.75 | L2 | 3.75 | Et3N | 0.75 | MAO/BHT | 3000 | — | 1 | 10 |
| 10 | CpTiCl3 | 0.25 | L2 | 2.5 | Et3N | 0.25 | MAO/BHT | 3000 | — | 1 | 10 |
| 12 | TiCl4 | 5 | — | — | Et3N | 10 | MAO/BHT | 250 | — | 1 | 10 |
| 13 | 3 | 5 | — | — | — | — | MAO/BHT | 250 | — | 1 | 10 |
| 14 | TiCl4 | 5 | L3 | 10 | Et3N | 10 | MAO/BHT | 250 | — | 1 | 10 |
| 15 | TiCl4 | 5 | L3 | 10 | — | — | MAO/BHT | 250 | — | 1 | 10 |

Metal-organic compound 1 = tris(N,N-dimethylamido)phosphoraneimido cyclopentadienyl titanium(IV) dichloride
Metal-organic compound 2 = 1,3-bis(2,6-dimethylphenyl)-iminoimidazoline cyclopentadienyl titanium dibenzyl
Metal-organic compound 3 = Bis(1-N-cyclohexylcarboximino-6-t-butylphenoxy)titaniumdichloride
L1 = N,N,N',N',N'',N''-hexamethylphosphorimidic triamide
L2 = 1,3-bis(2,6-dimethylphenyl)-iminoimidazoline
L3 = 1-N-cyclohexylcarboximine-6-t-butylphenol 2. Process according to claim 1, wherein the hydrocarbylating agent comprises a metal or a metalloid chosen from group 1, 2, 11, 12, 13 or 13.

3. Process according to claim 2, wherein the hydrocarbylating agent comprises Li, Mg, Zn or Al.

4. Process according to claim 3, wherein the hydrocarbylating agent is a $C_1$-$C_{20}$ trihydrocarbyl aluminum or aluminoxane.

5. Process according to claim 1, which further comprises conducting polymerization in the presence of a base other than the hydrocarbylating agent.

6. Process according to claim 1, wherein the metal-organic reagent comprises a cyclopentadienyl-comprising ligand.

7. Process according to claim 1, which comprising conducting polymerization in the presence of between 5 to 10 equivalents of the spectator ligand.

* * * * *